(12) United States Patent
Rifkin

(10) Patent No.: US 12,090,238 B2
(45) Date of Patent: Sep. 17, 2024

(54) COMPACT SANITIZING APPARATUS WITH OZONE AND ULTRAVIOLET FEATURES

(71) Applicant: Andrew B. Rifkin, San Pedro, CA (US)

(72) Inventor: Andrew B. Rifkin, San Pedro, CA (US)

( * ) Notice: Subject to any disclaimer, the term of this patent is extended or adjusted under 35 U.S.C. 154(b) by 408 days.

(21) Appl. No.: 17/604,984

(22) PCT Filed: Apr. 24, 2020

(86) PCT No.: PCT/US2020/029732
§ 371 (c)(1),
(2) Date: Oct. 19, 2021

(87) PCT Pub. No.: WO2020/219821
PCT Pub. Date: Oct. 29, 2020

(65) Prior Publication Data
US 2022/0249718 A1    Aug. 11, 2022

(51) Int. Cl.
| | | |
|---|---|---|
| *A61L 2/10* | (2006.01) | |
| *A47L 7/00* | (2006.01) | |
| *A47L 13/16* | (2006.01) | |
| *A47L 13/254* | (2006.01) | |
| *A47L 13/42* | (2006.01) | |
| *A61L 2/00* | (2006.01) | |
| *A61L 2/20* | (2006.01) | |

(52) U.S. Cl.
CPC .............. *A61L 2/10* (2013.01); *A47L 7/0061* (2013.01); *A47L 13/16* (2013.01); *A47L 13/254* (2013.01); *A47L 13/42* (2013.01); *A61L 2/202* (2013.01); *A47L 2201/00* (2013.01); *A61L 2202/11* (2013.01); *A61L 2202/122* (2013.01); *A61L 2202/14* (2013.01); *A61L 2202/17* (2013.01)

(58) Field of Classification Search
CPC ........ A61L 2/10; A61L 2/202; A61L 2202/11; A61L 2202/122; A61L 2202/14; A61L 2202/17; A47L 7/0061; A47L 3/16; A47L 3/254; A47L 3/42; A47L 2201/00
USPC ............................... 250/453.11, 454.11, 455
See application file for complete search history.

(56) References Cited

U.S. PATENT DOCUMENTS

2005/0000828 A1 *   1/2005   Carson .................. C02F 1/4672
                                                             205/703

* cited by examiner

*Primary Examiner* — Nicole M Ippolito
(74) *Attorney, Agent, or Firm* — Christopher J. Scott

(57) ABSTRACT

A compact, portable, low cost ultraviolet (UV) light source apparatus irradiates select or target surfacing for disinfecting or sanitizing the target surfacing or for decomposing ozone within a defined ozone environment. The ultraviolet light source apparatus according to the present invention essentially includes a power source; an ultraviolet (UV) light source in communication with the power source, and a mechanism for powering on and powering off the ultraviolet (UV) light source. The ultraviolet (UV) light source directs ultraviolet light toward a select surface for irradiating the surface or decomposing ozone. The ultraviolet (UV) light source apparatus may be attached to any number of select surfaces or objects or may be utilized to receive and hold objects for treating surfacing thereof.

15 Claims, 10 Drawing Sheets

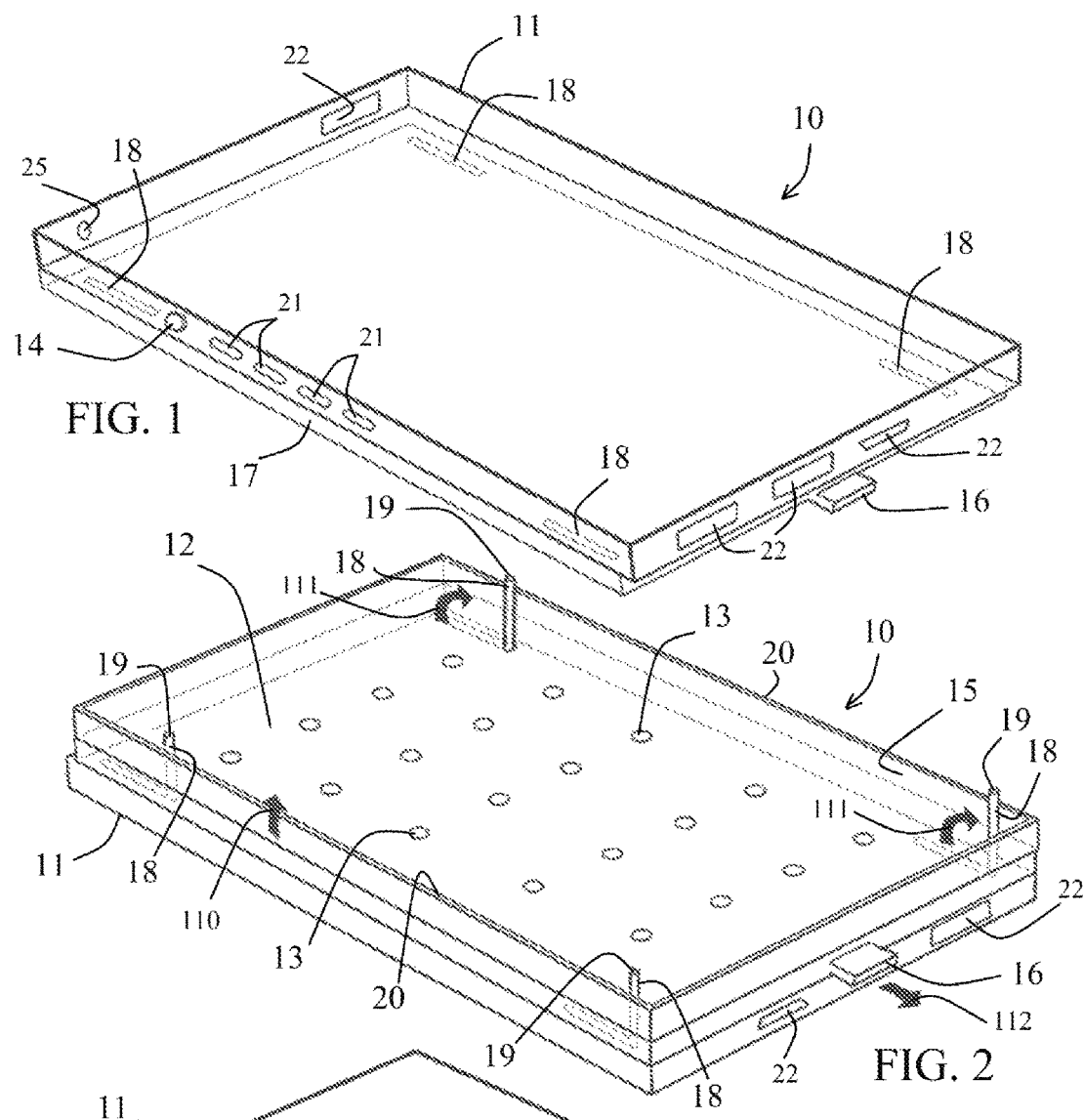
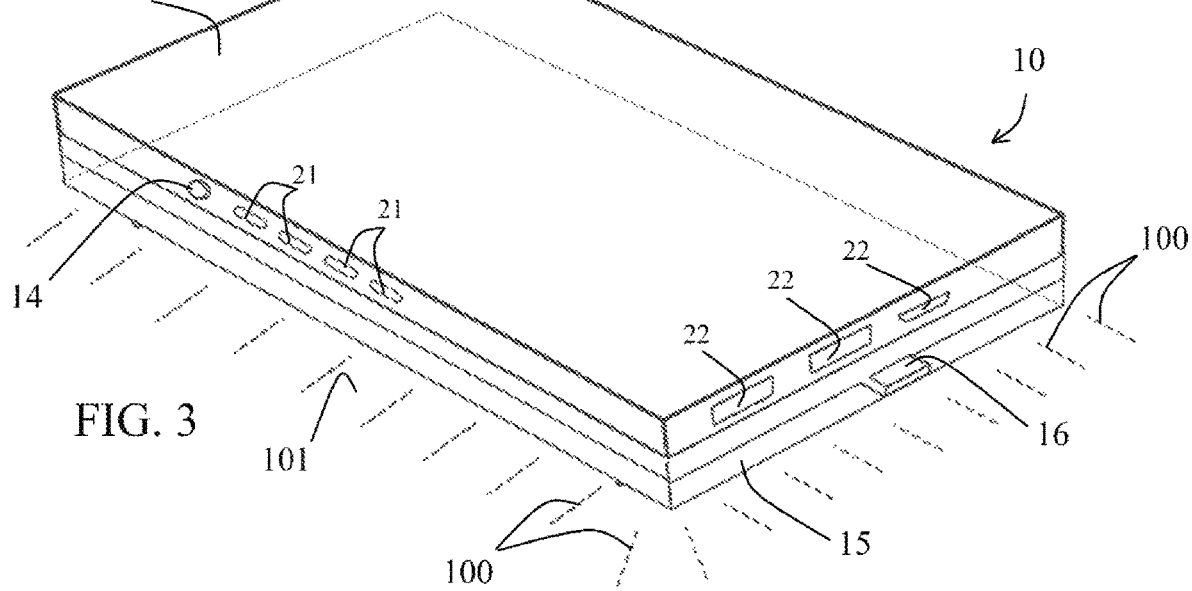

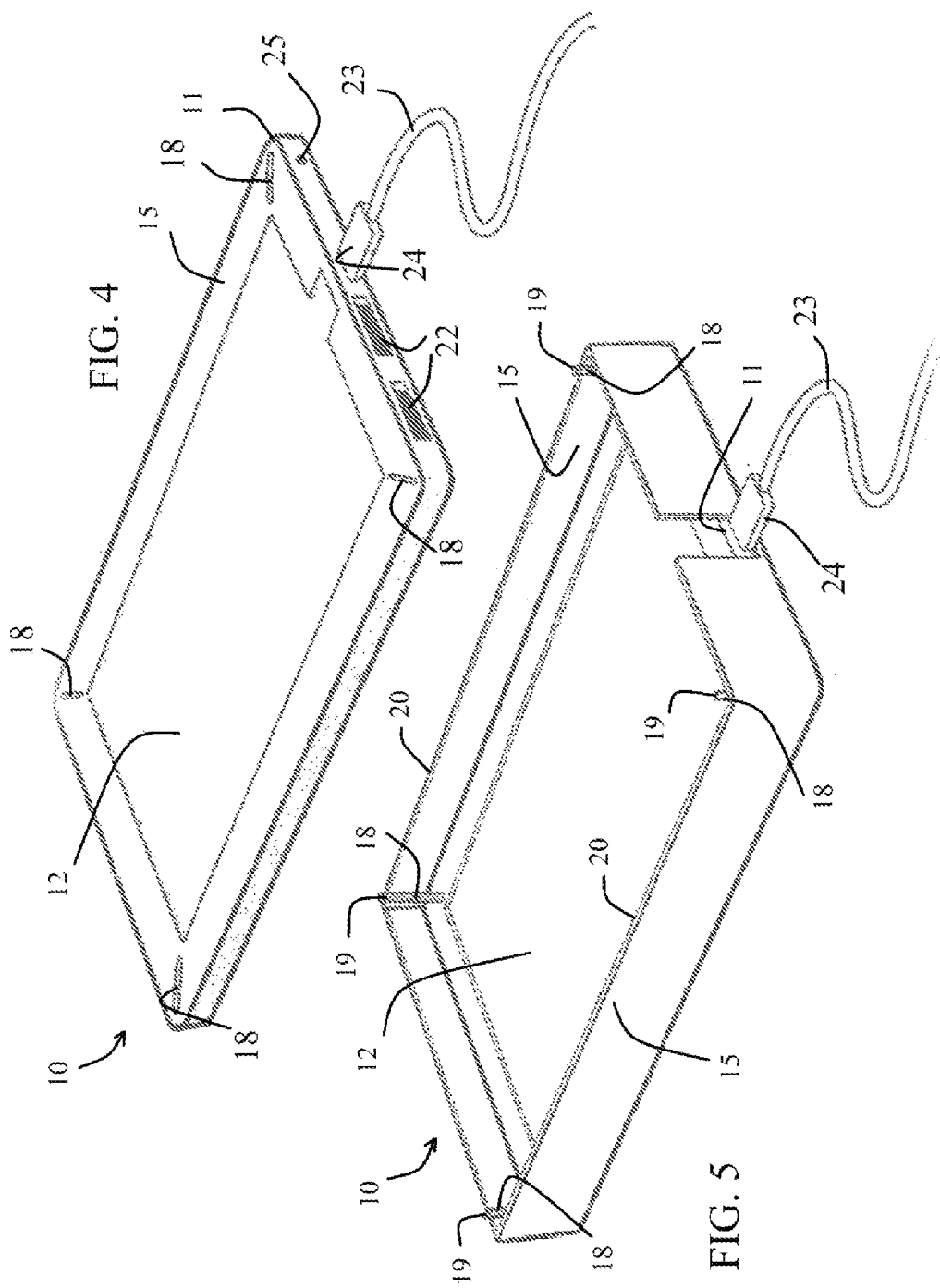

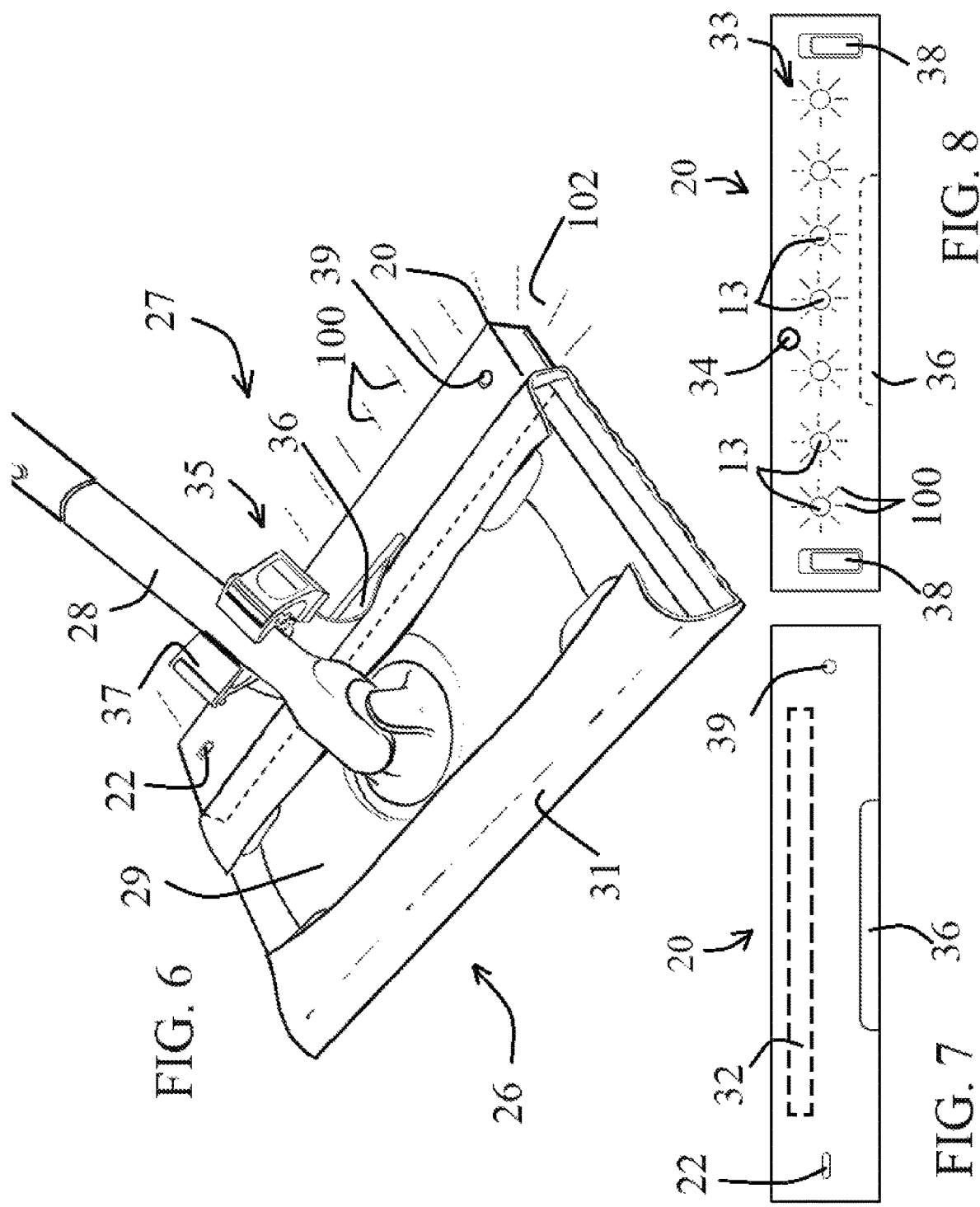

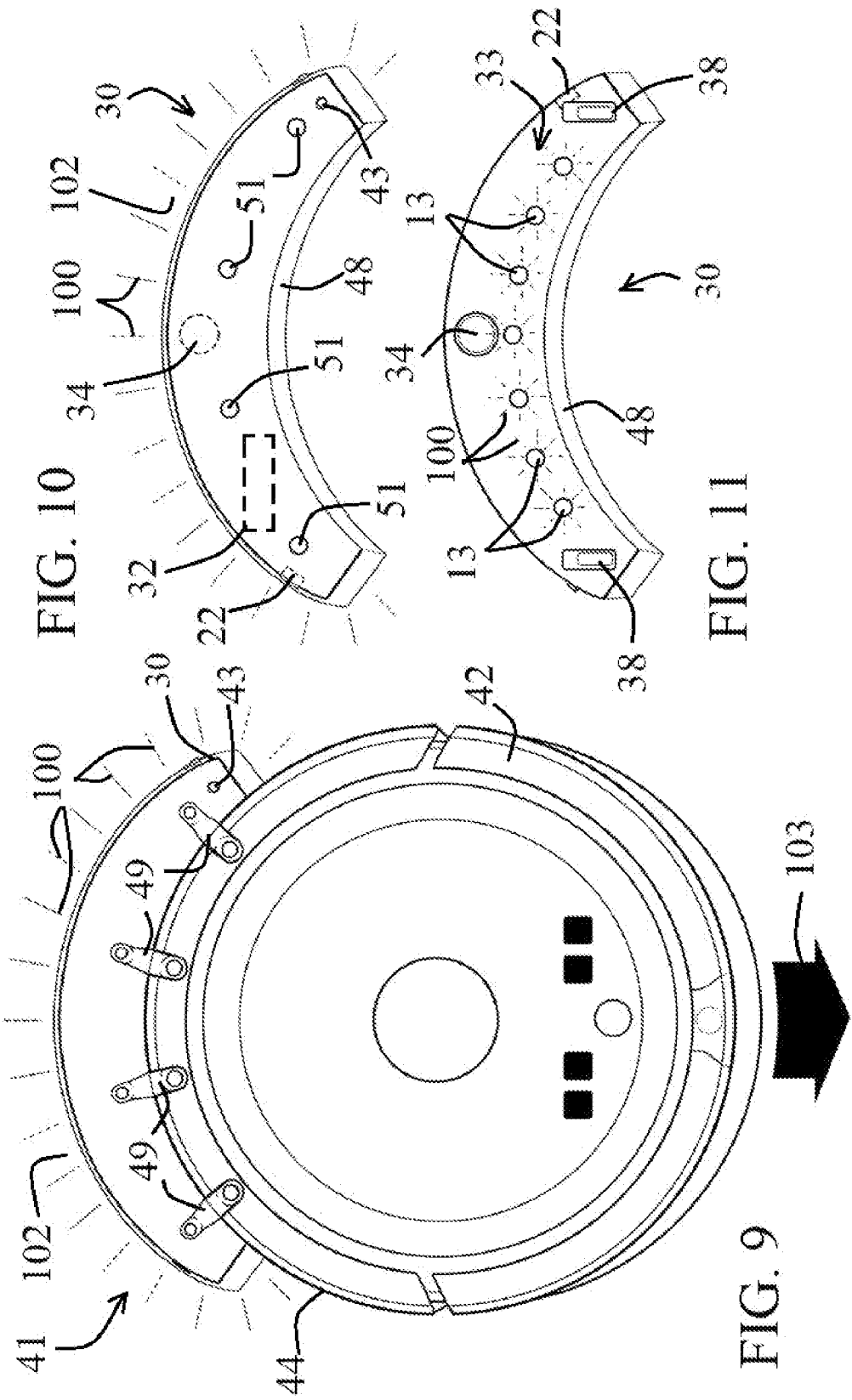

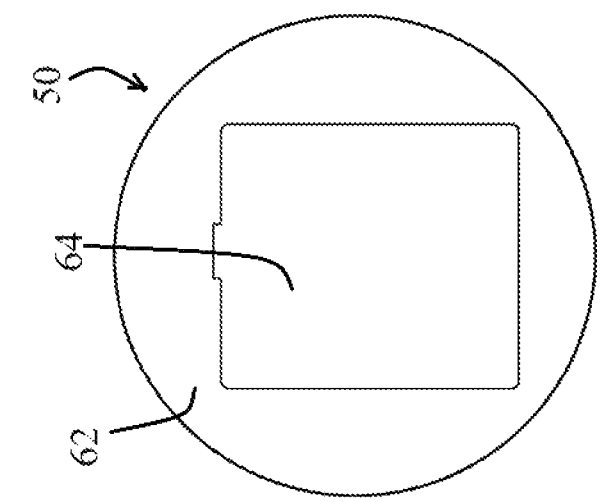
FIG. 17
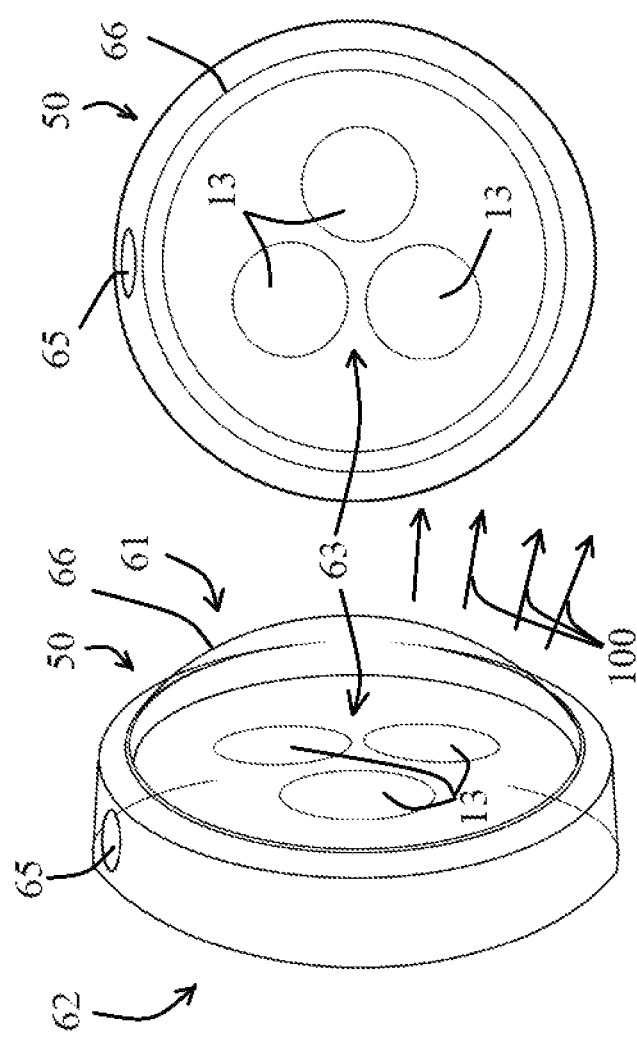
FIG. 16
FIG. 15

COMPACT SANITIZING APPARATUS WITH OZONE AND ULTRAVIOLET FEATURES

PRIOR HISTORY

This application is a US national stage entry application from International Patent Application No. PCT/US2020/029732 filed in the United States Patent and Trademark Office (USPTO) as International Receiving Office on 24 Apr. 2020, which International Patent application claims priority from U.S. Provisional Patent Application No. 62/838,224 filed in the USPTO on 24 Apr. 2019.

BACKGROUND OF THE INVENTION

Field of the Invention

The present invention generally relates to a compact or portable ultraviolet light source apparatus. More particularly, the present invention relates to a compact or portable ultraviolet light source apparatus attachable to or usable in combination with a plurality of peripheral or environmental objects for irradiating with ultraviolet light objects or surfaces in adjacency thereto or for decomposing ozone environments in which the objects or surfacing are situated.

Brief Description of the Prior Art

As is well understood in the art, ultraviolet light is a natural component of sunlight that can now be artificially produced through well proven solid-state technology. Ultraviolet light or UV light is mutagenic to bacteria, viruses, and other microorganisms, particularly at wavelengths around 260-270 nanometers or within the so-called UV-C spectrum. Ultraviolet germicidal irradiation harnesses the relatively short wavelengths within the Ultraviolet C or UV-C spectrum to kill or inactivate microorganisms by basically destroying nucleic acids and disrupting the DNA or microorganisms thereby disabling the microorganisms from performing cellular functions.

Ultraviolet germicidal irradiation or UVGI is used in variety of applications such as food, air, and water purification. The use of ozone within a defined environment in combination with ultraviolet (UV) irradiation has further been shown to be an effective sanitization treatment regimen. However, as has been reported in the prior art, these sanitation processes are typically not incorporated into storage containers or receptacles that allow for frequent access and frequent sanitation. Certain exemplary prior art applications generally discussing these generally concepts are briefly discussed hereinafter.

United States Patent Application Publication No. 2006/0278088, authored by Helsel, describes the use of ultraviolet light emitters within a vacuum cleaner comprising ultraviolet (UV) lights to neutralize bacterial contamination. The air and debris entering into the vacuum is exposed to one or more ultraviolet light sources, with the resulting radiation causing the bacterial contaminants to be neutralized. The vacuum used may be an upright bag vacuum, an upright bagless vacuum, a floor type vacuum, or a shop type vacuum. Multiple chambers are provided, in which the lights are disposed in secondary chambers, in addition to any lights used at the point of initial filtration.

United States Patent Application Publication No. 2016/0000950 ('950 Publication), authored by Won, discloses a Small Household Goods Sanitizing Apparatus. The '950 Publication describes an enclosure comprising a bottom open ended portion that serves to cover any of a variety of household goods. The top surface to the enclosure has a circuit formed of a switch, an ultraviolet (UV) light or lamp and battery to power the UV light or lamp. The UV light projects downward onto the enclosed household goods to sanitize the enclosed goods.

United States Patent Application Publication No. 2017/0072079, authored by Hecht et al, describes certain disinfecting devices and related methods that apply germicidal ultraviolet light to disinfect dispensing components of food and beverage dispensers. A disinfecting holster for a bar gun includes a support surface configured to interface with a bar gun to support the bar gun when stowed in the holster, a housing coupled with the support surface and surrounding a dispensing nozzle of the bar gun when the bar gun is stowed in the holster, and an ultraviolet light source configured to emit germicidal ultraviolet light onto the nozzle. The housing substantially contains the ultraviolet light within the housing during the application of the ultraviolet light to the dispensing nozzle. The ultraviolet light can be periodically applied to maintain the nozzle in a disinfected state.

United States Patent Application Publication No. 2018/0055960 ('960 Publication), authored by Reiber et al., discloses a Portable Disinfection Device. The '960 Publication describes a compact hands free, portable, rechargeable, waterproof, UV-C light emitting disinfection device. The disinfection device has a durable outer housing that holds an array of externally facing Ultraviolet C spectrum (UV-C) Light Emitting (LEDs) that emit light within the germicidal range of the Ultraviolet C spectrum or between the wavelength range of 200 nm to 280 nm. The disinfection unit can be deployed in a water bottle, backpack bladder, water jug, or any suitable container to disinfect water or other liquids.

United States Patent Application Publication No. 2019/0321502, authored by Kim et al. describes an apparatus for treating clothing having a cabinet in which a clothing accommodation space for accommodating clothing is formed; a housing detachably coupled to an inner wall of the clothing accommodation space and provided with a purifying space communicating with the clothing accommodation space; a photocatalyst containing a photocatalytic material and provided inside the housing; and a light source assembly, provided inside the housing, for irradiating light including UV rays by penetrating through the purifying space.

United States Patent Application Publication No. 2017/0096279, authored by Campalans et al. describes an apparatus, method and system for storing perishable items that degrade in the presence of oxygen and/or humidity and that are frequently accessed by a consumer. The apparatus comprises an openable vessel, which becomes airtight when closed, and an UV light source and fan within the airtight enclosure, which converts ambient oxygen trapped within the airtight enclosure into ozone by circulating the enclosed volume of air around the UV light source after the vessel is opened and then closed. The apparatus is network connected to allow for remote control and monitoring and sends alerts to web applications or mobile applications when monitored parameters substantially vary from their settings.

From a consideration of the foregoing, it will be noted that the prior art perceives a need for a low cost, portable ultraviolet (UV) light source apparatus for directing ultraviolet light toward select or target surfacing for irradiating the surfacing or decomposing an ozone environment in which the target surfacing is situated so as to provide a low cost solution for improving the overall safety of users as summarized in more detail hereinafter.

SUMMARY OF THE INVENTION

To achieve the aforementioned and other readily apparent objectives, the present invention essentially discloses in certain variants or embodiments a compact, portable, low cost ultraviolet (UV) light source apparatus for irradiating select or target surfacing or decomposing ozone within a defined environment for ozone-treating the select or target surfacing. A first ultraviolet light source apparatus according to the present invention is believed to essentially comprise a power bank portion having a power source; an ultraviolet (UV) light source matrix in communication with the power source, and means for powering on and powering off the ultraviolet (UV) light source matrix. The ultraviolet (UV) light source matrix directs ultraviolet light toward a select surface for irradiating said select surface.

The first ultraviolet (UV) light source apparatus may preferably comprise a retractable skirt mechanism. The retractable skirt mechanism extends peripherally about the ultraviolet (UV) light matrix and is configured (i) to be retracted when the ultraviolet (UV) light source matrix is in a powered-off state, and (ii) to be extended when the ultraviolet (UV) light source matrix is in a powered-on state. The retractable skirt mechanism is configured to space the ultraviolet (UV) light source matrix a distance from the select or target surface when in an extended state for preventing ambient light from entering a space defined by the select surface, the extended retractable skirt mechanism, and the ultraviolet (UV) light source matrix.

The first ultraviolet (UV) light source apparatus may further preferably comprise certain surface-sensing means for detecting the select or target surface and selectively powering off or powering on the ultraviolet (UV) light source matrix. The surface-sensing means may preferably be selected from a group consisting of a series of push pins, a series of pressure sensors, and/or a series of light sensors. An exemplary series of push pins are configured to extend in parallel relation to the ultraviolet (UV) light source matrix when in a powered-off state, and configured to extend orthogonally relative to the ultraviolet (UV) light source matrix when in a powered-on state.

The series of exemplary push pins comprise surface contact tips that extend past surface-opposing edging of the extended retractable skirt mechanism when the push pins are in a relaxed state. The series of push pins are actuable or axially displaceable toward the ultraviolet (UV) light source matrix by way of the select or target surface such that the surface contact tips may be displaced and become coplanar with the surface-opposing edging for selectively powering on the ultraviolet (UV) light source matrix and powering off the ultraviolet (UV) light source matrix when removed from the surface-actuated state.

A second ultraviolet (UV) light source apparatus according to the present invention is usable in combination with a floor mop so as to provide a floor mop-ultraviolet (UV) light source apparatus assembly. The floor mop-ultraviolet (UV) light source apparatus assembly according to the present invention comprises, in combination, a floor mop and the second ultraviolet (UV) light source apparatus. The floor mop essentially comprises a mop handle and a mop head coupled to the mop handle. The mop head is configured to hold a mopping element against a target floor surface.

The second ultraviolet (UV) light source apparatus essentially comprises a power source, an ultraviolet (UV) light source series in communication with the power source, and means for powering on and powering off the ultraviolet (UV) light source series. The ultraviolet (UV) light source apparatus may be mounted upon either the mop handle or the mop head and is configured to direct ultraviolet (UV) light upon the target floor surface for at least partially disinfecting the target floor surface adjacent the mop head.

The floor mop-ultraviolet (UV) light source apparatus assembly according to the present invention may further preferably comprise an apparatus-to-mop attachment mechanism. The apparatus-to-mop attachment mechanism preferably comprises an extension portion and a clip portion attached to the extension portion. The extension portion is affixed to the ultraviolet (UV) light source apparatus, and the clip portion preferably clips or clamps the extension portion to the mop handle.

The second ultraviolet (UV) light source apparatus of floor mop-ultraviolet (UV) light source apparatus assembly may further preferably comprises at least one, but preferably a pair of laterally opposed floor glides. The floor guides function to enhance movement of the ultraviolet (UV) light source apparatus upon the target floor surface.

The second mop-ultraviolet (UV) light source apparatus may further preferably comprise a floor surface contact sensor for detecting floor surface contact and (a) selectively powering on the ultraviolet (UV) light source series when the ultraviolet (UV) light source apparatus is placed into floor surface contact and (b) selectively powering off the ultraviolet (UV) light source series when removed from floor surface contact.

A third ultraviolet (UV) light source apparatus according to the present invention is usable in combination with a vacuum so as to provide a vacuum-ultraviolet (UV) light source apparatus assembly. The vacuum-ultraviolet (UV) light source apparatus assembly essentially comprises, in combination, a (robot) vacuum and the third ultraviolet (UV) light source apparatus. The vacuum essentially comprises an upper vacuum portion and a lower floor portion, which lower floor portion is configured to clean a target floor surface.

The third ultraviolet (UV) light source apparatus essentially comprises a power source, an ultraviolet (UV) light source series in communication with the power source, and means for powering on and powering off the ultraviolet (UV) light source series. The third ultraviolet (UV) light source apparatus is mounted upon the vacuum and configured to direct ultraviolet (UV) light upon the target floor surface for at least partially disinfecting the target floor surface adjacent the vacuum.

The robot vacuum may preferably comprises a circular housing. The circular housing has a housing circumference, which housing circumference has an outer apparatus attachment arc length section. The outer apparatus attachment arc length section has a vacuum radius of curvature. The arcuate third ultraviolet (UV) light source apparatus has an inner vacuum attachment arc length section having an apparatus radius of curvature. The vacuum radius of curvature and the apparatus radius of curvature are substantially equal such that the inner vacuum attachment arc length section abuts the outer apparatus attachment arc length section when the ultraviolet (UV) light source apparatus is mounted in radial outer adjacency to the vacuum.

The vacuum-ultraviolet (UV) light source apparatus assembly may further preferably comprise an apparatus-to-vacuum attachment mechanism, which apparatus-to-vacuum attachment mechanism couples the ultraviolet (UV) light source apparatus to the upper vacuum portion. The apparatus-to-vacuum attachment mechanism may preferably comprise a series of magnetic bridge connectors for magnetically attaching the ultraviolet (UV) light source apparatus to the vacuum.

The third ultraviolet (UV) light source apparatus of the vacuum-ultraviolet (UV) light source apparatus assembly may further preferably comprise at least one floor glide for enhancing movement of the third ultraviolet (UV) light source apparatus upon the target floor surface. Further, the third ultraviolet (UV) light source apparatus may further preferably comprise a floor surface contact sensor for detecting floor surface contact and (a) selectively powering on the ultraviolet (UV) light source series when the ultraviolet (UV) light source apparatus is placed into floor surface contact and (b) selectively powering off the ultraviolet (UV) light source series when removed from floor surface contact.

A fourth ultraviolet (UV) light source apparatus according to the present invention provides an ultraviolet (UV) light source sponge apparatus essentially comprising a sponge body, a power source, an ultraviolet (UV) light source in communication with the power source, and means for powering on and powering off the ultraviolet (UV) light source. The means for powering on and powering off the ultraviolet (UV) light source are preferably operable by compressing the sponge body. The ultraviolet (UV) light source is configured to direct ultraviolet (UV) light upon surfacing opposite the ultraviolet (UV) light source for at least partially disinfecting surfacing opposite the ultraviolet (UV) light source.

The ultraviolet (UV) light source sponge apparatus according to the present invention may further preferably comprise certain means for visually indicating apparatus-to-surface rate of motion. The means for visually indicating apparatus-to-surface rate of motion enhance a user's ability to at least partially disinfect surfacing opposite the ultraviolet (UV) light source by enabling the user to adjust his or her rate of motion of the apparatus when swiping the same over a target surface area.

A fifth ultraviolet (UV) light source apparatus according to the present invention essentially provides a puck style ultraviolet (UV) light source apparatus and is believed to essentially comprise an anterior portion, a posterior portion, a power source, an ultraviolet (UV) light source in communication with the power source, and means for powering on and powering off the ultraviolet (UV) light source. The ultraviolet (UV) light source is configured to direct ultraviolet (UV) light upon surfacing opposite the anterior portion for at least partially disinfecting the surfacing opposite the anterior portion.

The fifth ultraviolet (UV) light source apparatus may further preferably comprise a light sensor in communication with the ultraviolet (UV) light source. The light sensor detects changes in ambient light, powering on the ultraviolet (UV) light source when the ambient light is decreased below a threshold lumen value as, for example, when mounted within closed, low light spaces for irradiating surfacing within the closed space, and powering off the ultraviolet (UV) light source when the ambient light is increased above the threshold value as, for example, when the closed space is exposed. The anterior portion may be preferably characterized by comprising a transparent dome. The ultraviolet (UV) light source is preferably positioned in posterior adjacency to the transparent dome for directing ultraviolet (UV) light in an anterior direction relative to the posterior portion.

A sixth alternative ultraviolet (UV) light source apparatus according to the present invention is usable in combination with an ozone source thereby providing a combination ozone-ultraviolet (UV) light source apparatus. The combination ozone-ultraviolet (UV) light source apparatus according to the present invention essentially comprises an object-holding container and an object-sanitizing assembly cooperably associated with the object-holding container.

The object-holding container essentially comprises a compartment bottom portion and a bottom access portion as exemplified by a lid upper portion but alternatively and optionally defined by a door portion. It is contemplated that the bottom access portion is pivotally attached to the compartment bottom portion. The compartment bottom portion receives and holds objects to be sanitized. The bottom access portion selectively encloses the compartment bottom portion and enables a user to access objects held within the compartment bottom portion.

The object-sanitizing assembly essentially comprises a power source, an ultraviolet (UV) light source in communication with the power source, an ozone source in communication with the power source, and means for powering on and powering off (a) the ultraviolet (UV) light source and (b) the ozone source. The ozone source is configured to direct ozone into and circulate ozone within the object-holding container for sanitizing objects received and held within the object-holding container. The ultraviolet (UV) light source is configured to direct ultraviolet (UV) light into the object-holding container after ozone sanitization for decomposing ozone within the object-holding container.

The combination ozone-ultraviolet (UV) light source apparatus may further preferably comprise a liner assembly in communication with the ozone source for ozone containment within the object-holding container, and a rack within the liner assembly. The rack is supportable by way of the compartment bottom portion for supporting objects in elevated relation within the compartment bottom portion inside the liner assembly. The compartment bottom portion is preferably double wall-insulated for temperature stabilization within the object-holding container. The compartment bottom portion may further preferably comprises a space for receiving a weighted material. The compartment bottom portion may thus optionally weigh down the object-holding container when weighted material is received in the space for receiving the same.

BRIEF DESCRIPTION OF THE DRAWINGS

Other features of the invention will become more evident from a consideration of the following brief descriptions of patent drawings:

FIG. 1 is a posterior perspective view of a first alterative ultraviolet (UV) light source apparatus according to the present invention with a retractable skirt shown in a retracted state or configuration.

FIG. 2 is an anterior perspective view of the first alterative ultraviolet (UV) light source apparatus according to the present invention with the retractable skirt shown in an extended state or configuration with a first arrangement of surface contact pins shown in an extended state or configuration.

FIG. 3 is a posterior perspective view of the first alterative ultraviolet (UV) light source apparatus according to the present invention with the retractable skirt shown in the extended state of configuration for irradiating a select surface upon which the first alterative ultraviolet (UV) light source apparatus is positioned.

FIG. 4 is an anterior perspective view of the first alterative ultraviolet (UV) light source apparatus according to the present invention with the retractable skirt shown in a retracted state or configuration with a second arrangement of surface contact pins shown in a retracted state or configuration.

FIG. 5 is an anterior perspective view of the first alterative ultraviolet (UV) light source apparatus according to the present invention with the retractable skirt shown in an extended state or configuration with the second arrangement of surface contact pins shown in an extended state or configuration.

FIG. 6 is a perspective view of a second alternative ultraviolet (UV) light source apparatus according to the present invention as assembled in combination with a floor mop.

FIG. 7 is a top plan view of the second alternative ultraviolet (UV) light source apparatus according to the present invention with showing a fragmentary apparatus-to-mop attachment mechanism.

FIG. 8 is a bottom plan view of the second alternative ultraviolet (UV) light source apparatus according to the present invention.

FIG. 9 is a top perspective view of a third alternative ultraviolet (UV) light source apparatus according to the present invention in assembled relation with a robot type vacuum.

FIG. 10 is a top perspective view of the third alternative ultraviolet (UV) light source apparatus according to the present invention.

FIG. 11 is a bottom perspective view of the third alternative ultraviolet (UV) light source apparatus according to the present invention.

FIG. 15 is a perspective view of a fifth alternative ultraviolet (UV) light source apparatus according to the present invention.

FIG. 16 is an anterior plan view of the fifth alternative ultraviolet (UV) light source apparatus according to the present invention FIG. 17 is a posterior plan view of the fifth alternative ultraviolet (UV) light source apparatus according to the present invention.

DETAILED DESCRIPTION OF THE PREFERRED EMBODIMENTS

Figure 12:
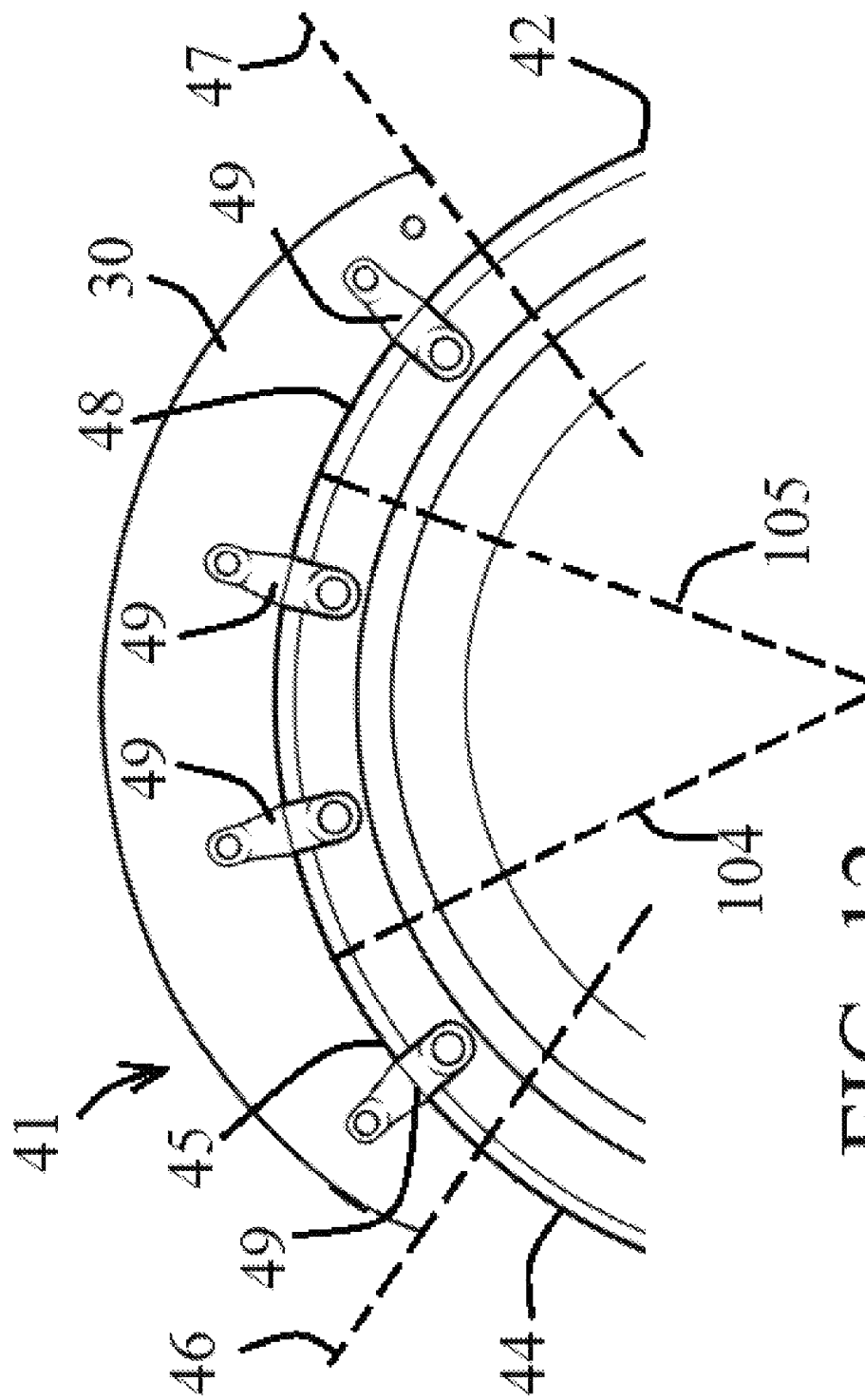
FIG. 12 is an enlarged top plan view of the third alternative ultraviolet (UV) light source apparatus according to the present invention in assembled relation with a fragmentary robot type vacuum highlighting the mated arcuate attachment interface between the third alternative ultraviolet (UV) light source apparatus and the robot type vacuum.

Referring now to the drawings with more specificity, the preferred embodiments of the present invention provide a series of compact, low cost ultraviolet (UV) light source apparatuses for irradiating select surfacing for primarily disinfecting or sanitizing the select surfacing as variously exemplified, or for secondarily decomposing an ozone environment in which the target surfacing is situated. In this regard, it is contemplated that the various ultraviolet (UV) light source apparatuses according to the present invention may be used to irradiate any number of surfaces, including, but not limited to airplane seats, tray tables, eating utensils, plates, computer input devices (e.g. computer keyboards), television remote controls, writing instruments, door knobs, hotel room bedding, head phones, touch screens, automatic teller machines or ATM's, fingerprint readers, vehicle interiors, children's toys and/or toy chests, books and magazines, floors, countertops, clothes hampers, cabinet interiors, drawer interiors, food boxes and similar containers, and lavatory surfacing, including toilet and sink surfacing and peripheral accessories such as toilet brushes and their containers.

A first alternative ultraviolet (UV) light source apparatus according to the present invention is generally depicted and referenced at 10 in FIGS. 1-5. The first alternative ultraviolet (UV) light source apparatus 10 is dimensioned or configured so as to be cooperable with a mobile communications device or case therefor and preferably comprises a power bank portion as at 11 and an ultraviolet (UV) light adaptor portion as at 17. The ultraviolet (UV) light adaptor portion 17 preferably comprises an ultraviolet (UV) light source matrix 12. The power bank portion 11 is essentially a rechargeable power source for powering the ultraviolet (UV) light source matrix 12. The ultraviolet (UV) light source matrix 12 preferably comprises a series of light emitting diodes or LED's as at 13 for emitting ultraviolet light preferably in the range or on the order of 260-270 nanometers or within the UV-C light band or spectrum.

The ultraviolet (UV) light source matrix 12 is in electrical communication with the power source of the power bank portion 11 and when powered on, the ultraviolet (UV) light source matrix 12 directs ultraviolet light (as at 100) of the preferred irradiating wavelength toward a select or target surface (as at 101) for irradiating the select or target surface 101 for disinfection or sanitization purposes. Certain means for powering on and powering off the ultraviolet (UV) light source matrix 12 are further contemplated as exemplified by an on-off button or switch as at 14.

The first ultraviolet (UV) light source apparatus 10 according to the present invention preferably further comprises a retractable skirt mechanism as at 15. The retractable skirt mechanism 15 preferably comprises a resilient, flexible (opaque) material construction such as silicone or similar material and extends peripherally about the ultraviolet (UV) light matrix 12. The retractable skirt mechanism 15 is preferably configured to be retracted when the ultraviolet (UV) light source matrix 12 is in a powered-off state as generally depicted in FIGS. 1 and 4; and is further configured to be extended as at vector 110 when the ultraviolet (UV) light source matrix 12 is in a powered-on state as generally depicted in FIGS. 2, 3, and 5.

It will thus be understood that the retractable skirt mechanism 15 is configured to space the ultraviolet (UV) light source matrix 12 a distance from the select surface 101 when in an extended state for preventing ambient light from entering a volumetric space defined by the plane of the select surface 101, the planes of the extended retractable skirt mechanism 15, and the plane of the ultraviolet (UV) light source matrix 12. It is contemplated that the retractable skirt mechanism 15 may be selectively extended by operation of a manual slide or pull type tab release as at 16. When manually operated to a skirt-release state as at vector 112, the tab release 16 operates to extend 110 the retractable skirt mechanism 15 to the extended state or configuration.

The first alternative ultraviolet (UV) light source apparatus 10 according to the present invention may further preferably comprise certain surface-sensing means for detecting or sensing contact with an underlying select or target surface 101. The surface-sensing means may be preferably exemplified by or selected from a group consisting of a series of push pin contacts or push pins (as depicted and referenced at 18), a series of pressure sensors (not specifically illustrated), and/or a series of light sensors (not specifically illustrated). When exemplary push pins 18 are provided, the series of push pins 18 are preferably configured to extend in parallel relation to the ultraviolet (UV) light source matrix 12 when in the powered off state as generally depicted in FIGS. 1 and 4, and further configured to extend as at arrows 111 orthogonally relative to the plane of the ultraviolet (UV) light source matrix 12 when in the powered-on state as generally depicted in FIGS. 2, 3, and 5.

The series of push pins 18 preferably comprise surface contact tips as at 19, which surface contact tips 19 extend past surface-opposing edging 67 of the extended retractable skirt mechanism 15. The series of push pins 18 are axially displaceable and/or depressable toward the ultraviolet (UV) light source matrix 12 by way of engagement with the select or target surface 101 such that the surface contact tips 19 are displaced into coplanar relation with the surface-opposing edging 67 for alternatively and selectively powering on the ultraviolet (UV) light source matrix 12 and powering off the ultraviolet (UV) light source matrix 12 when removed from the select or target surface 101.

The first alternative ultraviolet (UV) light source apparatus 10 according to the present invention may further preferably comprise a number of peripheral features that increase or enhance the functionality of the apparatus, including a series of light indicators as at 21 for visually indicating to the user the current state of the power source or how much power is stored in the power source or battery; a series of Universal Serial Bus or USB ports as at 22 for enabling the user to recharge the power source or battery by way of a power cord 23 outfitted with a USB connector head 24; and a visual indicator 25 for indicating to the user cycle time for ultraviolet (UV) light irradiation.

A second alternative ultraviolet (UV) light source apparatus according to the present invention is generally depicted and referenced at 20 and essentially provides an ultraviolet (UV) light bar for attachment to a common household floor mop 26 of the general type shown in FIG. 6. The second alternative ultraviolet (UV) light source apparatus 20 according to the present invention may thus be used in combination with a floor mop 26 for together providing a floor mop-ultraviolet (UV) light source apparatus assembly 27. In other words, the floor mop-ultraviolet (UV) light source apparatus assembly 27 according to the present invention may be said to preferably comprise, in combination, the floor mop 26 and the ultraviolet (UV) light source apparatus 20.

The floor mop 26 preferably comprises a mop handle as at 28, and a mop head 29 coupled to the mop handle 28, which mop head 29 is configured to hold a mopping element 31 against a floor surface as at 102. The ultraviolet (UV) light source apparatus 20 is preferably mounted upon either the mop handle 28 or the mop head 29 and configured to direct ultraviolet (UV) light 100 upon the floor surface 102 for at least partially disinfecting the floor surface 102 adjacent the mop head 29. The reader will note that the apparatus 20 is more effective at irradiating the floor surface if the apparatus 20, when piggybacked upon the floor mop 26, is displaced over the floor surface 102 at a relatively slower rate of speed, as discussed in more detail below.

The ultraviolet (UV) light source apparatus 20 preferably comprises a power source 32 as exemplified by either a rechargeable battery or a series of replacement batteries (e.g. four AA batteries). An ultraviolet (UV) light source series 33 is in communication with the power source 32 and positioned at a bottom portion of the ultraviolet (UV) light source apparatus 20. The ultraviolet (UV) light source series 33 comprises a series of light emitting diodes or LED's as at 13 for emitting ultraviolet light preferably in the range or on the order of 260-270 nanometers or within the UV-C light spectrum for directing ultraviolet light 100 toward the floor surface 102 for irradiating the floor surface 102.

The second alternative ultraviolet (UV) light source apparatus 20 further preferably comprises certain means for selectively powering on and powering off the ultraviolet (UV) light source series 33. The means for selectively powering on and powering off the ultraviolet (UV) light source apparatus 20 may be exemplified by a manually operated power button or switch and/or a floor surface contact/motion sensor as at 34. The floor surface contact/motion sensor 34 is preferably positioned upon the bottom portion of the ultraviolet (UV) light source apparatus 20 for detecting floor surface 102 contact for (a) selectively powering on the ultraviolet (UV) light source series 33 when the ultraviolet (UV) light source apparatus 20 is placed into floor surface 102 contact and (b) selectively powering off the ultraviolet (UV) light source series 33 when removed from floor surface 102 contact.

The floor mop-ultraviolet (UV) light source apparatus assembly 27 according to the present invention may further preferably comprise an apparatus-to-mop attachment mechanism as at 35. The apparatus-to-mop attachment mechanism 35 preferably comprises an extension portion 36 and a clamp or clip portion or head 37 attached to the extension portion 36. The extension portion 36 is preferably affixed to the ultraviolet (UV) light source apparatus 20 at a top portion thereof, and the clip portion or head 37 preferably and removably clips or clamps the extension portion 36 to the mop handle 28 as generally depicted in FIG. 6. The extension portion 36 preferably comprises or is constructed from a resilient material for rendering the extension portion 36 resiliently actuable or enhancing performance and fit adjacent the mop head 29. Further, the clip portion 37 is preferably adjustable for enabling enhanced fit with the mop handle 28.

The second alternative ultraviolet (UV) light source apparatus 20 according to the present invention may further preferably comprises at least one, but preferably a pair of laterally opposed floor glides as at 38. The floor guides 38 enhance movement of the bottom portion of the ultraviolet (UV) light source apparatus 20 as it travels upon the floor surface 102. The second alternative ultraviolet (UV) light source apparatus 20 may further preferably comprise a number of peripheral features that increase or enhance the functionality of the apparatus 20, including a flash light indicator 39 for visually indicating to the user the relative apparatus-to-floor rate of movement for enabling the user to more properly adjust the rate of apparatus movement relative to the floor surface 102. Further, a power or recharge port as at 22 enables the user to recharge the power source 32.

A third alternative ultraviolet (UV) light source apparatus according to the present invention is generally depicted and referenced at 30 and essentially provides an arcuate ultraviolet (UV) light bar for attachment to a robot vacuum 42 of the general type shown in FIG. 9. The third alternative ultraviolet (UV) light source apparatus 30 according to the present invention may thus be used in combination with a robot vacuum 42 for providing a vacuum-ultraviolet (UV) light source apparatus assembly 41. The vacuum-ultraviolet (UV) light source apparatus assembly 41 may be said to preferably comprise, in combination, the vacuum 42 and the third alternative ultraviolet (UV) light source apparatus 30.

The vacuum 42 preferably comprises an upper vacuum portion and a lower floor portion, the floor portion being configured to clean as at vector 103 a floor surface 102. The third alternative ultraviolet (UV) light source apparatus 30 preferably comprises at least one power source 32, but preferably at least two power sources 32, and an ultraviolet (UV) light source series 33 in communication with the power source 32. The ultraviolet (UV) light source series 33 is preferably positioned at a bottom portion of the third alternative ultraviolet (UV) light source apparatus 30. The ultraviolet (UV) light source series 33 preferably comprises a series of light emitting diodes or LED's as at 13 for emitting ultraviolet light preferably in the range or on the order of 260-270 nanometers or within the UV-C light spectrum for directing ultraviolet light 100 toward the floor surface 102 for irradiating the floor surface 102.

The third alternative ultraviolet (UV) light source apparatus 30 further preferably comprises means for powering on and powering off the ultraviolet (UV) light source series 33. The means for selectively powering on and powering off the ultraviolet (UV) light source apparatus 30 may be exemplified by a manually operated power button or switch as at 43 and/or a floor surface contact/motion sensor as at 34. The floor surface contact/motion sensor 34 is preferably positioned upon the bottom portion of the third alternative ultraviolet (UV) light source apparatus 30 for detecting floor surface 102 contact and (a) selectively powering on the ultraviolet (UV) light source series 33 when the ultraviolet (UV) light source apparatus 30 is placed into floor surface 102 contact and (b) selectively powering off the ultraviolet (UV) light source series 33 when removed from floor surface 102 contact.

The vacuum-ultraviolet (UV) light source apparatus assembly 41 according to the present invention may be further defined by incorporating a robot vacuum 42 having a circular housing as at 44, which circular housing 44 has a housing circumference. The housing circumference has a preferred apparatus attachment arc length section as at arcuate line/plane 45 extending between broken line 46 and broken line 47 in FIG. 12. The apparatus attachment arc length section 45 has a certain vacuum radius of curvature as at radius 104.

The third alternative ultraviolet (UV) light source apparatus 30 preferably further comprises an inner vacuum attachment arc length section as at arcuate line/plane 48 extending between broken line 46 and broken line 47. The inner vacuum attachment arc length section 48 preferably comprises a matching apparatus radius of curvature as at radius 105. In other words, the vacuum radius of curvature 104 and the apparatus radius of curvature 105 are preferably substantially equal such that the inner vacuum attachment arc length section 45 snugly abuts in mated engagement with the apparatus attachment arc length section 48 when the third alternative ultraviolet (UV) light source apparatus 30 is mounted in radial outer adjacency to the vacuum 42.

The vacuum-ultraviolet (UV) light source apparatus assembly 41 according to the present invention may further preferably comprise an apparatus-to-vacuum attachment mechanism, which apparatus-to-vacuum attachment mechanism operates to couple the third alternative ultraviolet (UV) light source apparatus 30 to the upper vacuum portion. The apparatus-to-vacuum attachment mechanism may preferably be defined by comprising a series of magnetic bridge connectors as at 49 for magnetically attaching the third alternative ultraviolet (UV) light source apparatus 30 to the vacuum 42. The magnetic bridge connectors 49 may be mounted to both the vacuum 42 and the third alternative ultraviolet (UV) light source apparatus 30 by way of mount apertures 51 as depicted on the third alternative ultraviolet (UV) light source apparatus 30 for ease of reference or understanding.

Similar to the floor mop-ultraviolet (UV) light source apparatus assembly 27, the third alternative ultraviolet (UV) light source apparatus 30 of the vacuum-ultraviolet (UV) light source apparatus assembly 41 may preferably comprise at least one floor glide 38, but preferably two laterally opposed floor guides 38 for enhancing movement of the third alternative ultraviolet (UV) light source apparatus 30 upon the floor surface 102. Further, the third alternative ultraviolet (UV) light source apparatus 30 may further preferably comprise a number of peripheral features that increase or enhance the functionality of the apparatus, including a power or recharge port as at 22 for enabling the user to recharge the power source 32.

Figure 13:
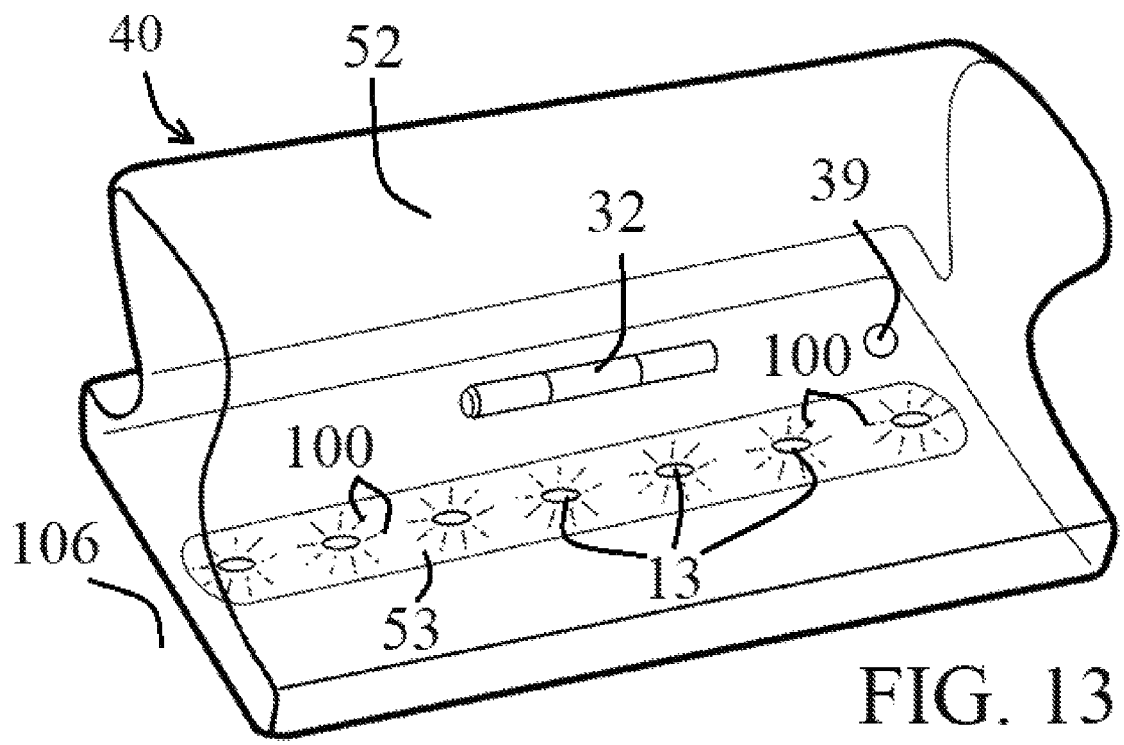
FIG. 13 is a top perspective view of a fourth alternative ultraviolet (UV) light source apparatus according to the present invention.
Figure 14:
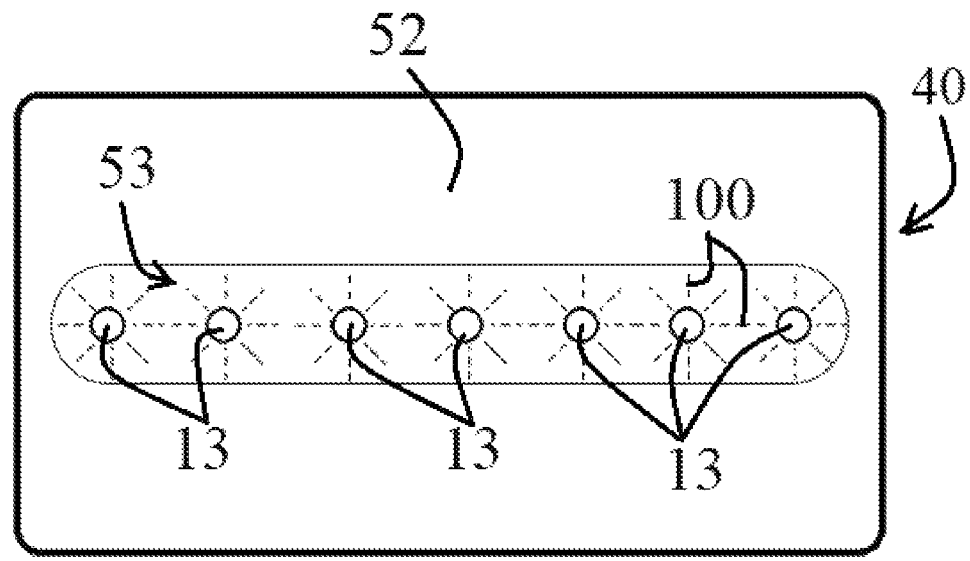
FIG. 14 is a bottom plan view of the fourth alternative ultraviolet (UV) light source apparatus according to the present invention.

A fourth alternative ultraviolet (UV) light source apparatus according to the present invention is generally depicted and referenced at 40 and essentially provides an ultraviolet (UV) sponge assembly or sponge apparatus of the general type shown in FIG. 13 that may have ultraviolet (UV) light activation when placed into contact with a select or target surface as at 106. The fourth alternative ultraviolet (UV) light source apparatus 40 preferably comprises a sponge body as at 52, an embedded power source as at 32, an ultraviolet (UV) light source matrix or series as at 53 positioned at a bottom portion of the sponge body 52 and in communication with the power source 32. Other optional peripheral features are contemplated that increase or enhance the functionality of the fourth alternative ultraviolet (UV) light source apparatus 40, including at least a flash light indicator 39 for visually indicating to the user the rate of sponge assembly or apparatus 40 movement relative to an underlying surface 106 (such as a countertop) for visually indicating to the user the proper rate of movement of the fourth alternative ultraviolet (UV) light source apparatus 40 relative to an underlying surface 106.

The ultraviolet (UV) light source series or matrix 53 preferably comprises a series of light emitting diodes or LED's as at 13 for emitting ultraviolet light preferably in the range or on the order of 260-270 nanometers or within the UV-C light spectrum for directing ultraviolet light 100 toward the underlying surface 106 for irradiating the underlying surface 106. The fourth alternative ultraviolet (UV) light source apparatus 40 further preferably comprises means for powering on and powering off the ultraviolet (UV) light source series or matrix 53. The means for selectively powering on and powering off the fourth alternative ultraviolet (UV) light source apparatus 40 may be exemplified by a manually operated power button or switch that operates to power on the apparatus 50 when the sponge body 52 is squeezed.

A fifth alternative ultraviolet (UV) light source apparatus according to the present invention is generally depicted and referenced at 50 and essentially provides a puck style ultraviolet (UV) light apparatus for attachment to any number of (planar) surfaces such as inside surfacing of clothes hampers, toy chests, insulated food boxes, folding boxes, cabinetry, pantries, refrigerators, garbage cans, and other similar areas typically closed off to light when in a closed state or configuration. The fifth alternative ultraviolet (UV) light source apparatus 50 operates to irradiate surfacing opposite the puck style apparatus 50 as comparatively depicted and referenced in FIGS. 15-17.

The fifth alternative ultraviolet (UV) light source apparatus 50 preferably comprises an anterior portion as at 61; a posterior portion as at 62; a power source exemplified by a series of AAA batteries received in a battery compartment 64 within the posterior portion 62; and an ultraviolet (UV) light source as at 63 comprising a series of light emitting diodes or LED's as at 13 for emitting ultraviolet light preferably in the range or on the order of 260-270 nanometers or within the UV-C light spectrum for directing ultraviolet light 100 toward select or target surfacing opposite the ultraviolet (UV) light source 63 for irradiating any such surfacing.

The fifth alternative ultraviolet (UV) light source apparatus 50 further preferably comprises certain means for powering on and powering off the ultraviolet (UV) light source 63 in electrical communication with the power source. The means for powering on and powering off the ultraviolet (UV) light source 63 are preferably exemplified by a light sensor 65 in further communication with the ultraviolet (UV) light source 63. The light sensor 65 operates to detect changes in ambient light, powering on the ultraviolet (UV) light source 63 when the ambient light is decreased below a threshold lumen value and powering off the ultraviolet (UV) light source 63 when the ambient light is increased above the threshold value.

The fifth alternative ultraviolet (UV) light source apparatus 50 may further preferably comprise certain means for attaching the posterior portion 62 to select surfacing opposite the target surfacing. In this regard, it is contemplated that the means for attaching the posterior portion 62 to select surfacing may be preferably exemplified or defined by self-stick adhesives. The anterior portion 61 may be further preferably characterized by comprising a transparent dome as at 66. It will be seen from a consideration of the drawings submitted in support of these specifications that the ultraviolet (UV) light source 63 is preferably positioned in posterior adjacency to the transparent dome 66 for directing ultraviolet (UV) light 100 generally in an anterior direction orthogonal relative to the posterior portion 63.

Figure 18:
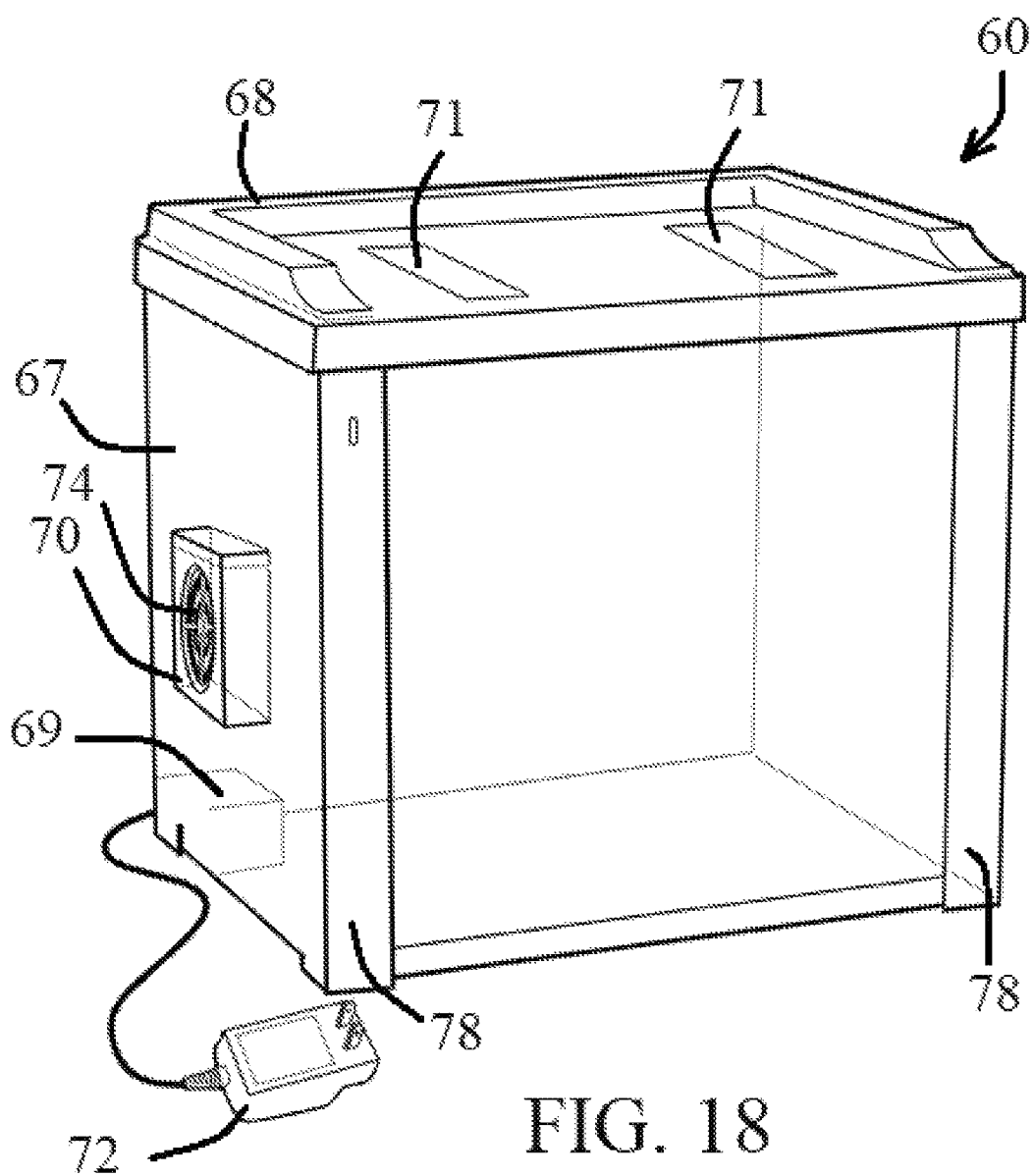
FIG. 18 is an anterior perspective view of a sixth alternative ultraviolet (UV) light source apparatus according to the present invention.
Figure 19:
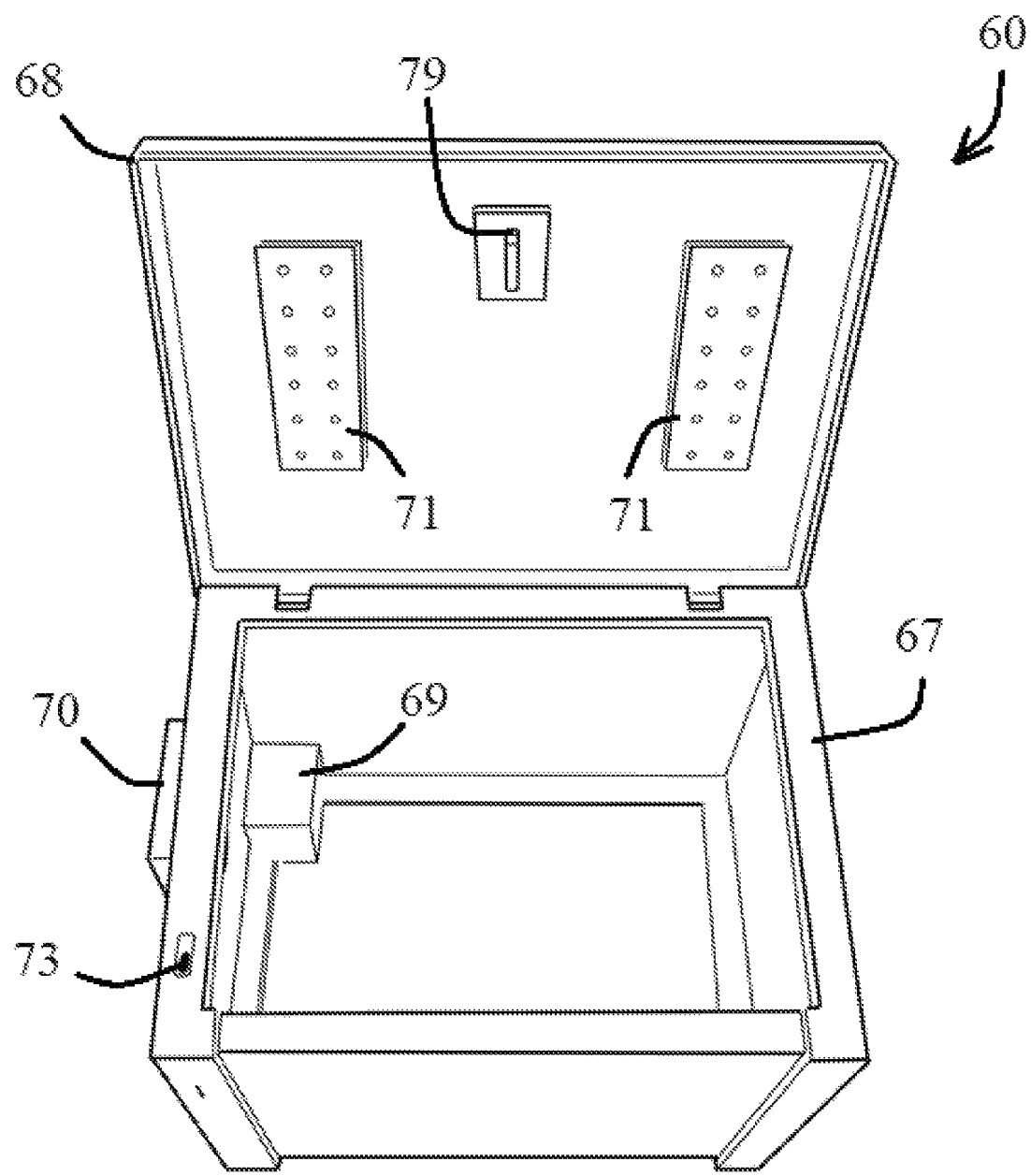
FIG. 19 is a first top perspective view of the sixth alternative ultraviolet (UV) light source apparatus according to the present invention showing essential component features of the sixth alternative ultraviolet (UV) light source apparatus.
Figure 20:
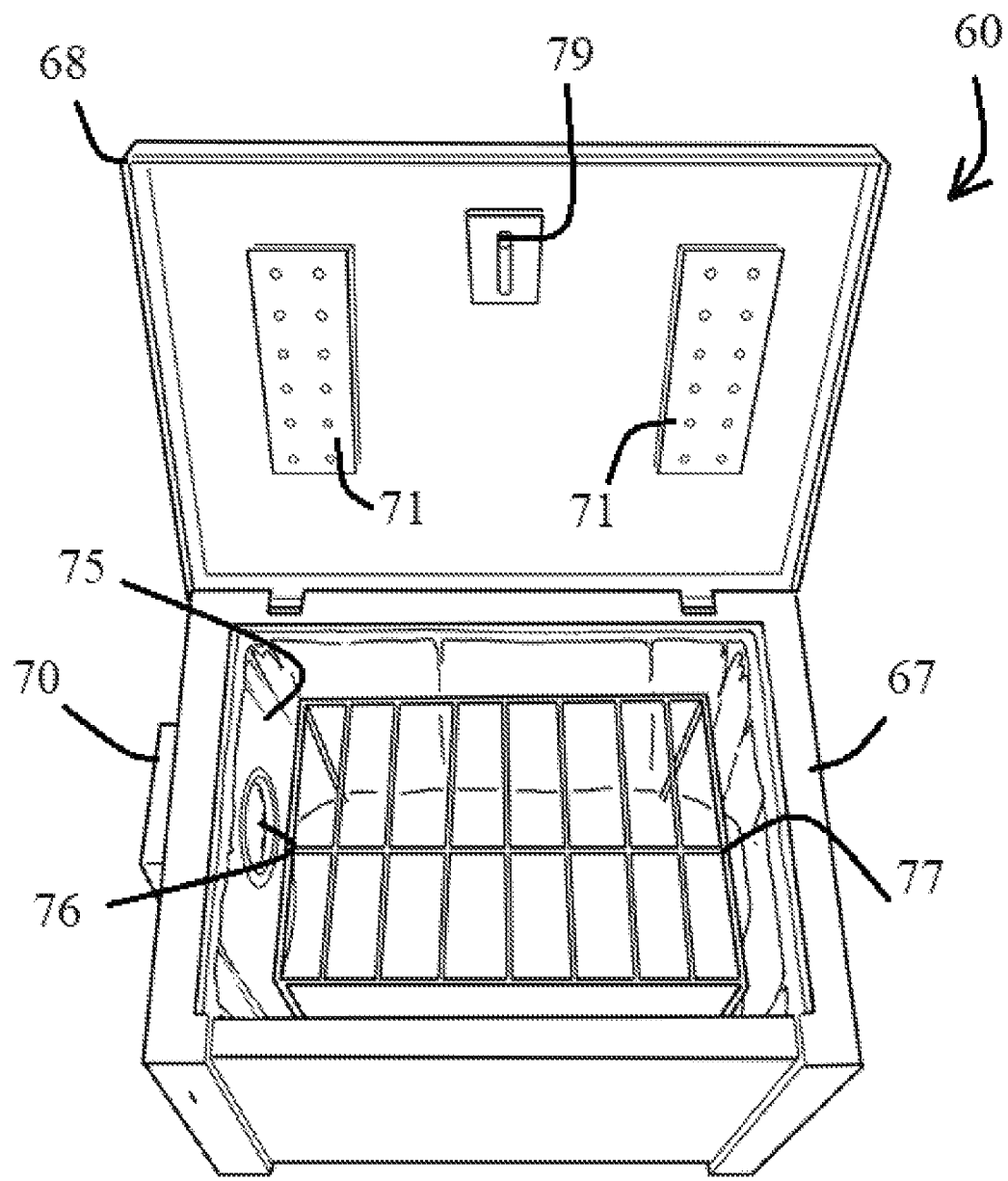
FIG. 20 is a second top perspective view of the sixth alternative ultraviolet (UV) light source apparatus according to the present invention showing both essential and optional component features of the sixth alternative ultraviolet (LTV) light source apparatus.

A sixth alternative ultraviolet (UV) light source apparatus 60 is generally depicted and referenced in FIGS. 18-20, which sixth alternative ultraviolet (UV) light source apparatus 60 is usable in combination with an ozone source for circulating ozone throughout an enclosed space within which objects to be sanitized may be received and held. In other words, the present invention further contemplates a combination ozone-ultraviolet (UV) light source apparatus as at 60. The combination ozone-ultraviolet (UV) light source apparatus 60 preferably comprises an object-holding container and an object-sanitizing assembly.

The object-holding container preferably comprises a compartment bottom portion 67 and a lid upper portion 68 pivotally attached to the compartment bottom portion 67. The compartment bottom portion 67 is dimensioned or configured to receive and hold objects to be sanitized as exemplified by packages, perishables or foodstuffs, and/or shoes. The lid upper portion 68 selectively covers the compartment bottom portion 67 and enables a user to access objects received and held within the compartment bottom portion 67.

The object-sanitizing assembly is cooperably associated with the object-holding container and comprises a series of components, including a power source (e.g. a rechargeable battery) 69; a multi-component module 70; at least one, but preferably two laterally opposed ultraviolet (UV) light source matrices as at 71; a battery charger 72; a latch control mechanism and/or door/lid-state detection sensor as at 73; and means for powering on and powering off (a) the ultraviolet light source matrices 71 and the ozone source. It is contemplated that the multi-component module 70 may well provide a fan 74 for ozone recirculation and venting, a flapper valve for ozone recirculation, an ozone generator or source, an electrical control system for controlling the fan 74, ozone source, and ultraviolet (UV) light source matrices 71, and battery-monitoring electronics.

The object-sanitizing assembly may thus be said to essentially comprise a power source, an ultraviolet (UV) light source in communication with the power source, an ozone source in communication with the power source, and means for powering on and powering off (a) the ultraviolet light source and (b) the ozone source. The ozone source is configured to direct ozone into and circulate ozone within the object-holding container for sanitizing objects received and held within the object-holding container. The ultraviolet (UV) light source or matrices 71 are configured to direct ultraviolet (UV) light into the object-holding container after ozone sanitization for decomposing ozone within the object-holding container.

The combination ozone-ultraviolet (UV) light source apparatus 60 may further preferably comprise a liner assembly 75 in communication with the ozone source for ozone containment within the object-holding container. The fan 74 vents ozone into the liner assembly 75 by way of an ozone inlet 76 formed in the liner assembly 75. A rack 77 may be further received within the liner assembly 75 and supported by way of the compartment bottom portion 67 for supporting objects (e.g. shoes) in elevated relation within the compartment bottom portion 67. The compartment bottom portion 67 is preferably double wall-insulated for temperature stabilization within the object-holding container.

Further, the compartment bottom portion 67 may preferably comprise a space as at 78 for receiving a weighted material (e.g. sand or water). The compartment bottom portion 67 may thus operate to weigh down the object-holding container when weighted material is received in the space 78 for receiving the same. An optional camera mount 79 is further contemplated and positioned upon the lid upper portion 68 for enabling a user to mount video surveillance camera for visually monitoring object-holding container activity.

The combination ozone-ultraviolet (UV) light source apparatus 60 may thus be utilized to receive and hold packages or foodstuffs or other objects to be sanitized. Once the apparatus 60 is activated by remote control, the disinfection/sanitization ozone gas cycle starts to run and the box or container latch is closed. It is contemplated that the cycle may run for approximately 30 minutes for packages and shoes, and approximately 15 minutes for foodstuffs. The latch system/mechanism and sensor switch together operate to terminate the ozone source or generator if the lid/door (i.e. bottom access portion) is opened. The rechargeable batteries used in combination with the apparatus 60 are contemplated to last 7 days before recharging with normal use.

The liner assembly may be lifted out of the lower bottom portion easily for transporting disinfected/sanitized objects into other areas such as the home or residence. After the ozone disinfection/sanitization cycle, the air inside the object-holding container is treated with ultraviolet (UV) light for ozone decomposition or by way of an ozone destructive catalyst before the air is vented out to remove the ozone residue. Once final ventilation is complete, the latch mechanism is deactivated and the bottom access portion may be opened to enable the user to access the contents. The bottom of the apparatus 60 may be filled with weighted material such as sand or water or both to weigh down the apparatus and help prevent movement of the apparatus 60. The camera mount allows a user to use a wireless video camera to track or monitor individuals accessing the apparatus 60.

While the above descriptions contain much specificity, this specificity should not be construed as limitations on the scope of the invention, but rather as an exemplification of the invention. In certain embodiments, the basic invention may be said to essentially teach or disclose a number of ultraviolet (UV) light source apparatuses for irradiating select or target surfacing. A first ultraviolet light source apparatus according to the present invention is believed to essentially comprise a power bank portion having a power source; an ultraviolet (UV) light source matrix in communication with the power source, and means for powering on and powering off the ultraviolet (UV) light source matrix. The ultraviolet (UV) light source matrix directs ultraviolet light toward a select surface for irradiating said select surface.

The first ultraviolet (UV) light source apparatus preferably further comprises a retractable skirt mechanism. The retractable skirt mechanism extends peripherally about the ultraviolet (UV) light matrix and is configured to be retracted when the ultraviolet (UV) light source matrix is in a powered-off state, and is configured to be extended when the ultraviolet (UV) light source matrix is in a powered-on state. The retractable skirt mechanism is configured to space the ultraviolet (UV) light source matrix a distance from the select or target surface when in an extended state and prevent ambient light from entering a space defined by the select surface, the extended retractable skirt mechanism, and the ultraviolet (UV) light source matrix.

The first ultraviolet (UV) light source apparatus may further preferably comprise certain surface-sensing means for detecting the select or target surface and selectively powering off or powering on the ultraviolet (UV) light source matrix. The surface-sensing means may preferably be selected from a group consisting of a series of push pins, a series of pressure sensors, and/or a series of light sensors. The exemplary series of push pins are configured to extend in parallel relation to the ultraviolet (UV) light source matrix when in a powered-off state, and configured to extend orthogonally relative to the ultraviolet (UV) light source matrix when in a powered-on state.

The series of push pins comprise surface contact tips that extend past surface-opposing edging of the extended retractable skirt mechanism when in a relaxed state. The series of push pins are actuable or axially displaceable toward the ultraviolet (UV) light source matrix by way of the select surface such that the surface contact tips may be displaced so as to become coplanar with the surface-opposing edging for selectively powering on the ultraviolet (UV) light source matrix and powering off the ultraviolet (UV) light source matrix when removed from the select or target surface.

A second ultraviolet (UV) light source apparatus according to the present invention is usable in combination with a floor mop so as to provide a floor mop-ultraviolet (UV) light source apparatus assembly. The floor mop-ultraviolet (UV) light source apparatus assembly according to the present invention comprises, in combination, a floor mop and the second ultraviolet (UV) light source apparatus. The floor mop essentially comprises a mop handle and a mop head coupled to the mop handle. The mop head is configured to hold a mopping element against a target floor surface.

The second ultraviolet (UV) light source apparatus essentially comprises a power source, an ultraviolet (UV) light source series in communication with the power source, and means for powering on and powering off the ultraviolet (UV) light source series. The ultraviolet (UV) light source apparatus may be mounted upon either the mop handle or the mop head and is configured to direct ultraviolet (UV) light upon the target floor surface for at least partially disinfecting the floor surface adjacent the mop head.

The floor mop-ultraviolet (UV) light source apparatus assembly according to the present invention may further preferably comprise an apparatus-to-mop attachment mechanism. The apparatus-to-mop attachment mechanism preferably comprises an extension portion and a clip portion attached to the extension portion. The extension portion is affixed to the ultraviolet (UV) light source apparatus, and the clip portion preferably clips or clamps the extension portion to the mop handle.

The second ultraviolet (UV) light source apparatus of floor mop-ultraviolet (UV) light source apparatus assembly may further preferably comprises at least one, but preferably a pair of laterally opposed floor glides. The floor guides function to enhance movement of the ultraviolet (UV) light source apparatus upon the target floor surface. The second mop-ultraviolet (UV) light source apparatus may further preferably comprise a floor surface contact sensor for detecting floor surface contact and (a) selectively powering on the ultraviolet (UV) light source series when the ultraviolet (UV) light source apparatus is placed into floor surface contact and (b) selectively powering off the ultraviolet (UV) light source series when removed from floor surface contact.

A third ultraviolet (UV) light source apparatus according to the present invention is usable in combination with a vacuum so as to provide a vacuum-ultraviolet (UV) light source apparatus assembly. The vacuum-ultraviolet (UV) light source apparatus assembly essentially comprises, in combination, a (robot) vacuum and the third ultraviolet (UV) light source apparatus. The vacuum essentially comprises an upper vacuum portion and a lower floor portion, which lower floor portion is configured to clean a target floor surface.

The third ultraviolet (UV) light source apparatus essentially comprises a power source, an ultraviolet (UV) light source series in communication with the power source, and means for powering on and powering off the ultraviolet (UV) light source series. The third ultraviolet (UV) light source apparatus is mounted upon the vacuum and configured to direct ultraviolet (UV) light upon the target floor surface for at least partially disinfecting the target floor surface adjacent the vacuum.

The robot vacuum may preferably comprises a circular housing as has become relatively standardized in the industry. The circular housing has a housing circumference, which housing circumference has an outer apparatus attachment arc length section. The outer apparatus attachment arc length section has a vacuum radius of curvature. The arcuate third ultraviolet (UV) light source apparatus has an inner vacuum attachment arc length section having an apparatus radius of curvature. The vacuum radius of curvature and the apparatus radius of curvature are substantially equal such that the inner vacuum attachment arc length section abuts the outer apparatus attachment arc length section when the ultraviolet (UV) light source apparatus is mounted in radial outer adjacency to the vacuum.

The vacuum-ultraviolet (UV) light source apparatus assembly may further preferably comprise an apparatus-to-vacuum attachment mechanism, which apparatus-to-vacuum attachment mechanism couples the ultraviolet (UV) light source apparatus to the upper vacuum portion. The apparatus-to-vacuum attachment mechanism comprises a series of magnetic bridge connectors for magnetically attaching the ultraviolet (UV) light source apparatus to the vacuum.

The third ultraviolet (UV) light source apparatus of the vacuum-ultraviolet (UV) light source apparatus assembly may further preferably comprise at least one floor glide for enhancing movement of the third ultraviolet (UV) light source apparatus upon the target floor surface. Further, the third ultraviolet (UV) light source apparatus may further preferably comprise a floor surface contact sensor for detecting floor surface contact and (a) selectively powering on the ultraviolet (UV) light source series when the ultraviolet (UV) light source apparatus is placed into floor surface contact and (b) selectively powering off the ultraviolet (UV) light source series when removed from floor surface contact.

A fourth ultraviolet (UV) light source apparatus according to the present invention provides an ultraviolet (UV) light source sponge apparatus essentially comprising a sponge body, a power source, an ultraviolet (UV) light source in communication with the power source, and means for powering on and powering off the ultraviolet (UV) light source. The means for powering on and powering off the ultraviolet (UV) light source are preferably operable by compressing the sponge body. The ultraviolet (UV) light source is configured to direct ultraviolet (UV) light upon surfacing opposite the ultraviolet (UV) light source for at least partially disinfecting surfacing opposite the ultraviolet (UV) light source.

The ultraviolet (UV) light source sponge apparatus according to the present invention may further preferably comprise certain means for visually indicating apparatus-to-surface rate of motion. The means for visually indicating apparatus-to-surface rate of motion enhance a user's ability to at least partially disinfect surfacing opposite the ultraviolet (UV) light source by enabling the user to adjust his or her rate of motion of the apparatus when swiping the same over a target surface area.

A fifth ultraviolet (UV) light source apparatus according to the present invention essentially provides a puck style ultraviolet (UV) light source apparatus and is believed to essentially comprise an anterior portion, a posterior portion, a power source, an ultraviolet (UV) light source in communication with the power source, and means for powering on and powering off the ultraviolet (UV) light source. The ultraviolet (UV) light source is configured to direct ultraviolet (UV) light upon surfacing opposite the anterior portion for at least partially disinfecting the surfacing opposite the anterior portion.

The fifth ultraviolet (UV) light source apparatus may further preferably comprise a light sensor in communication with the ultraviolet (UV) light source. The light sensor detects changes in ambient light, powering on the ultraviolet (UV) light source when the ambient light is decreased below a threshold lumen value and powering off the ultraviolet (UV) light source when the ambient light is increased above the threshold value, as for example, when mounted within closed spaces for irradiating surfacing within the closed space. The anterior portion may be preferably characterized by comprising a transparent dome. The ultraviolet (UV) light source is preferably positioned in posterior adjacency to the transparent dome for directing ultraviolet (UV) light in an anterior direction relative to the posterior portion.

A sixth alternative ultraviolet (UV) light source apparatus according to the present invention is usable in combination with an ozone source thereby providing a combination ozone-ultraviolet (UV) light source apparatus. The combination ozone-ultraviolet (UV) light source apparatus according to the present invention essentially comprises an object-holding container and an object-sanitizing assembly cooperably associated with the object-holding container.

The object-holding container essentially comprises a compartment bottom portion and a bottom access portion as exemplified by the lid upper portion but alternatively and optionally defined by a door portion. It is contemplated that the bottom access portion is pivotally attached to the compartment bottom portion. The compartment bottom portion receives and holds objects to be sanitized. The bottom access portion selectively encloses the compartment bottom portion and enables a user to access objects held within the compartment bottom portion.

The object-sanitizing assembly essentially comprises a power source, an ultraviolet (UV) light source in communication with the power source, an ozone source in communication with the power source, and means for powering on and powering off (a) the ultraviolet (UV) light source and (b) the ozone source. The ozone source is configured to direct ozone into and circulate ozone within the object-holding container for sanitizing objects received and held within the object-holding container. The ultraviolet (UV) light source is configured to direct ultraviolet (UV) light into the object-holding container after ozone sanitization for decomposing ozone within the object-holding container.

The combination ozone-ultraviolet (UV) light source apparatus may further preferably comprise a liner assembly in communication with the ozone source for ozone containment within the object-holding container, and a rack within the liner assembly. The rack is supportable by way of the compartment bottom portion for supporting objects in elevated relation within the compartment bottom portion inside the liner assembly. The compartment bottom portion is preferably double wall-insulated for temperature stabilization within the object-holding container. The compartment bottom portion may further preferably comprises a space for receiving a weighted material. The compartment bottom portion may thus optionally weigh down the object-holding container when weighted material is received in the space for receiving the same.

What is claimed is:

1. A combination ozone-ultraviolet (UV) light source apparatus, the combination ozone-ultraviolet (UV) light source apparatus comprising:
    an object-holding container, the object-holding container comprising a compartment bottom portion and a lid upper portion pivotally attached to the compartment bottom portion, the compartment bottom portion for receiving and holding objects to be sanitized, the lid upper portion for selectively covering the compartment bottom portion and enabling a user to access objects held within the compartment bottom portion; and an object-sanitizing assembly cooperably associated with the object-holding container, the object-sanitizing assembly comprising a power source, an ultraviolet (UV) light source in communication with the power source, an ozone source in communication with the power source, a liner assembly, and means for powering on and powering off (a) the ultraviolet (UV) light source and (b) the ozone source, the ozone source being configured to direct ozone into and circulate ozone within the object-holding container for sanitizing objects held within the object-holding container, the liner assembly being in communication with the ozone source for ozone containment within the object-holding container, the ultraviolet (UV) light source being configured to direct ultraviolet (UV) light into the object-holding container after ozone sanitization for decomposing ozone within the object-holding container.

2. The combination ozone-ultraviolet (UV) light source apparatus of claim 1 comprising a rack within the liner assembly, the rack being supportable by way of the compartment bottom portion for supporting objects in elevated relation within the compartment bottom portion inside the liner assembly.

3. The combination ozone-ultraviolet (UV) light source apparatus of claim 2 wherein the compartment bottom portion is double wall-insulated for temperature stabilization within the object-holding container.

4. The combination ozone-ultraviolet (UV) light source apparatus of claim 3 wherein the compartment bottom portion comprises a space for receiving a weighted material, the compartment bottom portion for weighing down the object-holding container when weighted material is received in the space for receiving the weighted material.

5. The combination ozone-ultraviolet (UV) light source apparatus of claim 1 wherein the ultraviolet (UV) light source comprises laterally opposed light source matrices, the laterally opposed light source matrices being mounted on the lid upper portion for directing laterally opposed ultraviolet (UV) light into the compartment bottom portion for enhancing ozone decomposition within the object-holding container.

6. The combination ozone-ultraviolet (UV) light source apparatus of claim 1 comprising a multi-component module, the multi-component module comprising a fan and flapper valve for ozone recirculation and venting, ozone being recirculated to cycle past objects held within the object-holding container for enhancing ozone contact therewith.

7. The combination ozone-ultraviolet (UV) light source apparatus of claim 6 wherein the fan vents ozone into the liner assembly by way of an ozone inlet formed in the liner assembly.

8. An ozone apparatus for sanitizing objects held therewithin, the ozone comprising:

an object-holding container, the object-holding container comprising a compartment bottom portion and a lid upper portion pivotally attached to the compartment bottom portion, the compartment bottom portion for receiving and holding objects to be sanitized, the lid upper portion for selectively covering the compartment bottom portion and enabling a user to access objects held within the compartment bottom portion; and an object-sanitizing assembly cooperably associated with the object-holding container, the object-sanitizing assembly comprising a power source, an ozone source in communication with the power source, a liner assembly, and means for powering on and powering off the ozone source, the ozone source being configured to direct ozone into and circulate ozone within the object-holding container for sanitizing objects held within the object-holding container, the liner assembly being in communication with the ozone source for ozone containment within the object-holding container.

9. The ozone apparatus according to claim 8 comprising a rack within the liner assembly, the rack being supportable by way of the compartment bottom portion for supporting objects in elevated relation within the compartment bottom portion inside the liner assembly.

10. The ozone apparatus according to claim 9, wherein the compartment bottom portion is double wall-insulated for temperature stabilization within the object-holding container.

11. The ozone apparatus according to claim 10, wherein the compartment bottom portion comprises a space for receiving a weighted material, the compartment bottom portion for weighing down the object-holding container when weighted material is received in the space for receiving the weighted material.

12. The ozone apparatus according to claim 8 comprising an ultraviolet (UV) light source in communication with the power source and means for powering on and powering off the ultraviolet (UV) light source, the ultraviolet (UV) light source being configured to direct ultraviolet (UV) light into the object-holding container after ozone sanitization for decomposing ozone within the object-holding container.

13. The ozone apparatus according to claim 12, wherein the ultraviolet (UV) light source comprises laterally opposed light source matrices, the laterally opposed light source matrices being mounted on the lid upper portion for directing laterally opposed ultraviolet (UV) light into the compartment bottom portion for enhancing ozone decomposition within the object-holding container.

14. The ozone apparatus according to claim 8 comprising a multi-component module, the multi-component module comprising a fan and flapper valve for ozone recirculation and venting, ozone being recirculated to cycle past objects held within the object-holding container for enhancing ozone contact therewith.

15. The ozone apparatus according to claim 14, wherein the fan vents ozone into the liner assembly by way of an ozone inlet formed in the liner assembly.

* * * * *